United States Patent [19]
Peng et al.

[11] Patent Number: 5,858,329
[45] Date of Patent: Jan. 12, 1999

[54] MRI DIAGNOSTIC PROCEDURES USING TRIPODAL PYRIDINYL METAL COMPLEXES

[75] Inventors: Wei-Jen Peng; Humberto Ramos, Jr., both of Corpus Christi, Tex.

[73] Assignee: Hoechst Celanese Corporation, Corpus Christi, Tex.

[21] Appl. No.: 916,126

[22] Filed: Aug. 21, 1997

[51] Int. Cl.$^6$ .......................... A61B 5/055; A61K 51/00; C07D 401/00
[52] U.S. Cl. .................... 424/9.361; 424/9.36; 424/1.65; 546/2; 546/5; 546/268.1; 546/261
[58] Field of Search ................. 424/9.361, 9.36, 424/9.364, 9.3, 1.65; 534/10, 14, 15, 16; 546/2, 5, 6, 261, 263, 264, 265, 266, 268.1; 540/465, 471; 544/63, 124; 548/101

[56] References Cited

U.S. PATENT DOCUMENTS

| | | |
|---|---|---|
| 4,001,323 | 1/1977 | Felder et al. . |
| 4,250,113 | 2/1981 | Nordal et al. . |
| 4,396,598 | 8/1983 | Lin . |
| 4,647,447 | 3/1987 | Gries et al. . |
| 4,687,658 | 8/1987 | Quay . |
| 4,687,659 | 8/1987 | Quay . |
| 4,719,098 | 1/1988 | Weinmann et al. . |
| 4,826,673 | 5/1989 | Dean et al. . |
| 4,837,169 | 6/1989 | Toner . |
| 4,957,939 | 9/1990 | Gries et al. . |
| 4,960,895 | 10/1990 | Ohkawa . |
| 5,130,437 | 7/1992 | Rocklage et al. . |
| 5,216,134 | 6/1993 | Mukkala et al. . |
| 5,252,740 | 10/1993 | Hale et al. . |
| 5,405,601 | 4/1995 | Dunn et al. . |
| 5,457,186 | 10/1995 | Mukkala et al. . |
| 5,559,214 | 9/1996 | Delecki et al. . |
| 5,571,897 | 11/1996 | Takalo et al. . |
| 5,608,059 | 3/1997 | Wear et al. . |
| 5,624,901 | 4/1997 | Raymond et al. . |

OTHER PUBLICATIONS

Chemical Communications, Number 14 (1992), Adolfsson et al.
Chemical Communications, Number 22 (1992), Adolfsson et al.
Organic Chemistry, Fourth Edition of T.W. Graham Solomons, 1988.

*Primary Examiner*—José G. Dees
*Assistant Examiner*—Michael G. Hartley
*Attorney, Agent, or Firm*—James J. Mullen; Depaoli & Frenkel

[57] ABSTRACT

A method of performing an NMR diagnostic procedure in a patient in need of the same comprising administering to the patient an effective amount of an NMR diagnostic medium and then exposing the patient to an NMR measurement step to which the diagnostic medium is responsive thereby imaging at least a portion of the patient's body, wherein the diagnostic medium comprises a composition of matter which contains a compound which has the structural formula:

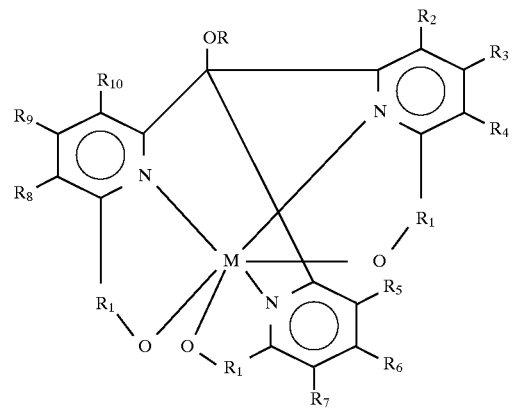

wherein R, $R_1$–$R_{10}$ and M are defined herein.

20 Claims, No Drawings

MRI DIAGNOSTIC PROCEDURES USING TRIPODAL PYRIDINYL METAL COMPLEXES

FIELD OF THE INVENTION

This invention relates to magnetic resonance imaging (MRI), X-ray imaging, and radiopharmaceuticals. More particularly the invention relates to methods and compositions for enhancing MRI, X-ray imaging, and radiopharmaceuticals, ligands therefor and precursors of said ligands.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast of internal organs and tissues may be obtained by administering compositions containing paramagnetic metal species which increase the relaxation rate of surrounding protons. In ultrasound diagnostics, improved contrast is obtained by administering compositions having acoustic impedances different than that of blood or other tissues.

The recently developed technique of MRI encompasses the detection of certain atomic nuclei utilizing magnetic fields and radio-frequency radiation. It is similar in some respects to x-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that it has found application as a means of mapping the internal structure of the body as a result of the original suggestion of Lauterbur (Nature, 242, 190–191 ([1973]). The fundamental lack of any known hazard associated with the level of magnetic and radio-frequency fields that are employed renders it possible to make repeated scan of vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin when placed in an applied magnetic field (B, expressed generally in units of gauss or Tesla [$10^4$ gauss]) align in the direction of the field. In the case of protons, these nuclei precess at a frequency, f, of 42.6 MHZ, at a field strength of 1 Tesla. At this frequency, an RF pulse of radiation will excite the nuclei and can be considered to tip the net magnetization of the field direction, the extent of this rotation being determined by the pulse duration and energy. After the RF pulse, the nuclei "relax" or return to equilibrium with the magnetic field, emitting radiation at the resonant frequency. The decay of the emitted radiation characterized by two relaxation times, i.e., $T_1$, the spin-lattice relaxation time or longitudinal relaxation time, that is, the time taken by the nuclei to return to equilibrium along the direction the externally applied magnetic field, and $T_2$, the spin-spin relaxation time associated with dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density pulse sequence and flow) may contribute to the MRI signal.

By reason of its sensitivity to subtle physiochemical differences between tissue types in detecting diseases which induce physiochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic number of 21 to 29, 42 to 44 and 58 to 70 have been found effective as MRI contrasting agents. Examples of suitable ions include chromium (III), manganese (II), manganese (III), iron (II), iron (III), cobalt (II), nickel (II), copper (II), praseodymium (III), neodymium (III), samarium (III), and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

Typically, paramagnetic ions have been administered in the form of complexes with organic complexing agents. Such complexes provide the paramagnetic ion in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gried et al. is the complex of gadolinium (III) with diethylenetriamine-pentaacetic acid ("DTPA"). Paramagnetic ions, such as gadolinium (III), have been found to form strong complexes with DTPA, ethylenediamine-tetraacetic acid ("EDTA"), and with tetraazacyclododecane-N,N',N",N'''-tetraacetic acid ("DOTA").

These complexes do not dissociate substantially in physiological aqueous fluids. The gadolinium complex of DTPA has a net charge of −2, whereas the gadolinium complex of EDTA or DOTA has a net charge of −1, and both are generally administered as soluble salts. Typical salts are sodium and N-methylglucamine. The administration of salt is attended by certain disadvantages. These salts can raise the in vivo ion concentration and cause localized disturbances in osmolality, which in turn, can lead to edema and other undesirable reactions.

Efforts have been made to design new ionic and neutral paramagnetic metals complexes which avoid or minimize the above mentioned disadvantages. In general, this goal can be achieved by converting one or more of the free carboxylic acid groups of the complexing agents to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxyalkylamide derivatives of DTPA and their use as complexing agents for paramagnetic ions. It can also be achieved by covalent attachment of organic cations of the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al. AJR 142, 679 (March 1984) and Brasch, et al. AJR, 142,625 (March 1984).

Finally, toxicity of paramagnetic metal complexes is greatly affected by the nature of the complexing agents. In vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Caheris et al., *Magnetic Resonance Imaging*, 8:467 (1990) and Oksendal, et al., *JMRI*, 3:157 (1993).

A need continues to exist for new and structurally diverse compounds for use as imaging agents including ligands therefor and precursor ligands. There is a further need to develop highly stable complexes with good relaxivity and osmolar characteristics.

Thus, there is always a need for new and more effective agents requiring lower dosage use, lower toxicity, higher resolution and more organ/disease specificity.

DESCRIPTION OF THE PRIOR ART

The following prior art references are disclosed for informational purposes.

U.S. Pat. No. 4,001,323 discloses water-soluble non-ionizing hydroxy-containing amide derivatives of 2,4,6-triiodoisophthalic acid for use as radiopaque materials.

U.S. Pat. No. 4,250,113 discloses new amides as X-ray contrast agents.

U.S. Pat. No. 4,396,598 discloses triiodoisophthalamide X-ray contrast agents.

U.S. Pat. No. 4,647,447 discloses new paramagnetic contrast agents.

U.S. Pat. No. 4,687,659 discloses homologs of diamide-DTPA-paramagnetic compounds as contrast agents for MR imaging.

U.S. Pat. No. 4,719,098 discloses enteral contrast medium useful for nuclear magnetic resonance.

U.S. Pat. No. 4,885,363 discloses 1-substituted-1,4,7-triscarboxymethyl-1,4,7,10-tetraazacyclododecane useful when complexed with a paramagnetic metal atom as MR imaging agents.

U.S. Pat. No. 4,916,246 discloses paramagnetic chelates useful for NMR imaging.

U.S. Pat. No. 4,957,939 discloses sterile pharmaceutical compositions of gadolinium chelates useful as enhancing NMR imaging.

U.S. Pat. No. 5,405,601 discloses functionalized tripodal ligands for imaging applications.

*Proc. Natl. Acad. Sci.* USA, Vol 93. pp 6610–6615, June 1996, Medical Sciences; Young et al. disclose gadolinium (III) texaphyrin: a tumor selective radiation sensitizer that is detectable by MRI.

H. Reimlinge, *Chem. Be.*, 92, 970 (1995) discloses synthesis of substituted pyrazoles.

Kamitori Y. et al, *Heterocycles*, 38 (1), 21 (1994) discloses synthesis of substituted pyrazoles.

Sauer, D. R. et al., *Carbohyde Res.*, 241 (1993) 71 discloses synthesis of substituted pyrazoles.

Amoroso, A. J. et al, *J. Chem. Soc., Chem. Comm.* 1994, 2751, discloses a general synthesis of ligands.

Campbell, A. D. et al., *Aust. J. Chem.* 1971, 24, 377–83 discloses a general synthesis of ligands.

Kametani, T., *Tetrahedron*, 1970, 26, 5753 discloses a general synthesis of ligands. All of the above cited prior art and any other references mentioned herein are incorporated herein by reference in their entirety.

SUMMARY OF THE INVENTION

The present invention provides novel compositions of matter having the formulae:

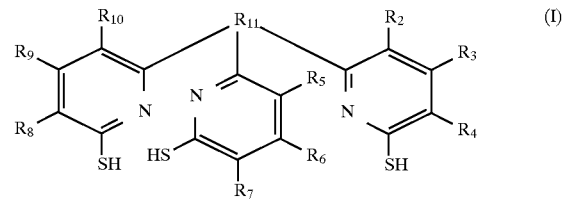

(I)

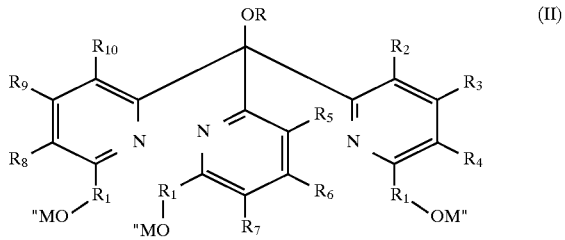

(II)

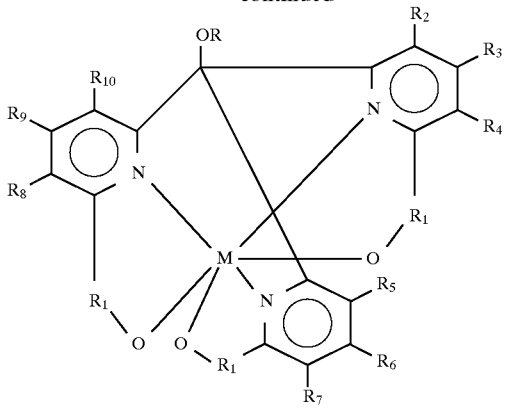

(III)

wherein R, $R_1$–$R_{11}$, M and M" of formulae I, II, and III are defined herein, for example, as MRI contrasting agents.

Compositions comprising the above formula (III) wherein M is a radioactive metal ion, a paramagnetic ion, or a metal ion capable of absorbing X-rays are also provided for use as radiopharmaceuticals, magnetic resonance imaging, and X-ray contrast agents, respectively.

Diagnostic compositions comprising the compounds of the invention are also provided. Methods of performing diagnostic procedures with compositions of the inventions are also disclosed. The methods comprise administering to a patient an effective amount of compositions of the invention and subjecting the patient to an imaging procedure.

DETAILED DESCRIPTION OF THE INVENTION

There is provided, in one part of the present invention, new and structurally diverse compositions of matter having the formulae set forth above and identified as I, II, and III, and wherein:

$R_1$ is S or SO $R_2$–$R_{10}$ are each independently selected from the group consisting of
  (a) R
  (b) OR
  (c) $N(R)_2$
  (d) NHC(O)R
  (e) $COO^-M'$
  (f) $C(O)N(R)_2$, and
  (g) $SO_3^-M'$
  wherein R is selected from the group consisting of
    (i) H
    (ii) $C_1$–$C_{20}$ alkyl
    (iii) hydroxyalkyl ($C_1$–$C_{30}$)
    (iv) $CH_2CH(OH)CH_2(O\ CH_2CH(OH)CH_2)_nOH$(n= 0–10)
    (v) $CH_2CH_2(O\ CH_2CH_2)_nOH$ (n=0–10)
    (vi) ribose
    (vii) glucose
    (viii) peptide or polypeptide
    (ix) $PO_3^{2-}\ 2M'$
    and M' is $Na^+$ or meglumine $R_{11}$ is COR or P M" is Li, Na or K, and and M is a suitable metal ion such as a metal ion of the lanthanide series having an atomic number of 57–71 or a transition metal of an atomic number of 21–29, 42, or 44.

In the above formula III, M is selected from the group consisting of chromium (III), manganese (II), iron (III), iron (II), cobalt (II), nickel (II), copper (II), praseodymium (III), neodymium (III), samarium (III), ytterbium (III), gadolinium (III), terbium (III), dysprosium (III), holmium (III), erbium (III), lanthamium (III), gold (III), lead (II), bismuth (III), lutetium (III), and europium (III).

Examples of suitable alkyl groups for use with the invention include methyl, ethyl, propyl, isopropyl, butyl, cyclohexyl, heptyl, and octyl. Suitable alkoxy groups include methoxy, ethoxy, propoxy, butoxy, pentoxy, hexoxy, heptoxy, and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris (hydroxymethyl)methyl and 2-hydroxy-1-hydroxymethylethyl. Suitable alkoxyalkyl groups include methoxymethyl, 2,3-dimethoxypropyl, tris(methoxymethyl)methyl, and 2-methoxy-1-methoxymethyl-ethyl.

The compositions of formula III are suitable for use with a variety of modalities including X-rays, magnetic resonance imaging and radiopharmaceuticals.

The functionality of the $R_2$–$R_{10}$ groups of the compositions of formula III of the present inventions afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies, a fragment of monoclonal antibody and aptamers. Specific examples of biomolecules include insulins, prostaglandins, growth factors, liposomes and nucleic acid probes. Examples of synthetic polymers include polylysine, arborols, dendrimers, cyclodextrins. The advantages of using biomolecules include enhanced tissue targeting through specificity and delivery. Coupling of the chelating moieties to biomolecules can be accomplished by several known methods (e.g., Krejacarek and Tucke Biochem. *Biophys. Rs. Comm.*, 30, 581 (1977); Hantowich, et al. *Science,* 220, 613 (1983). For example, a reactive moiety present in one of the $R_2$–$R_{10}$ groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols, and hydrazines. Electrophilic group examples include halides, disulfides, epoxides, maleimides, acid chlorides, anhydrides, mixed anhydrides, activated esters, imidates, isocyanates and isothiocyanates. And finally, the compositions of formula III should provide the additional advantage of being kinetically inert.

The present invention composition of formula III with one of more central metal ions or metal ion equivalents (M), such as paramagnetic metals praseodymium (III), neodymium (III), samarium (III), ytterbium (III) terbium (III), dysprosium (III), holmium (III), erbium (III), iron (II), iron (III), chromium(III), cobalt (II) and nickel (II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, the novel composition of formula III are relatively substantially nontoxic and therefore useful for enhancing magnetic resonance images by favorably altering relaxation times $T_1$ and $T_2$ and affording improved contrast between normal and diseased tissues or organs.

The preferred compositions of formula III are those formed with iron (II), iron (III), manganese (II), manganese (III), lutetium (III) and gadolinium (III) as the central metal ion or ions (M). Depending upon the particular ligand employed and the particular central metal ion used (M), the compositions formed may be neutral, ionic, cationic, or zwitterionic in nature, or they may be negatively charged. The neutral compositions are generally preferred and generally appear to exhibit relatively lower toxicity as compared to ionic or negatively charged compositions. The negatively charged compositions formed by the ligands and central metal ions enumerated above may be further complexed with one or more cations of an inorganic or organic base which are physiologically tolerated. Examples of cations for further complexing include sodium, potassium, calcium, and salts of N-methylglucamine, an diethanolamine.

In addition to their utility in magnetic resonance imaging procedures, the compositions of formula III can also be employed for delivery of either radiopharmaceuticals or heavy metals for X-ray contrast into the body. For use in diagnostic and therapeutic radiopharmaceuticals the complexed metal ion (M) must be radioactive. Radioisotopes of the elements technetium, rhenium, indium, gallium, copper, ytterbium, samarium and holmium are suitable. For use as X-ray contrast applications the complexed metal ion (M) must be able to absorb adequate amounts of the X-rays. These metal ions are generally referred to as radiopaque. Suitable elements for use as the radiopague metal ion include lead, bismuth, gadolinium, dysprosium, holmium and praseodymium.

The compositions of formula III can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M or a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, nontoxic cations. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution of suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of MR image. Such dose may vary widely, depending upon the particular paramagnetic ion complex employed, the organs or tissues which are subject of the imaging procedure, the MR imaging procedure, the MR imaging equipment being used, and the like. In general, parenteral dosages will range from about 0.001 to about 1.0 mmol of paramagnetic ion complex per kg of patient body weight. Preferred parenteral dosages generally range from about 0.01 to about 0.5 mmol of paramagnetic ion complex per kg of patient body weight. Enteral dosages generally range from about 0.5 to about 100 mmol, preferable from about 1.0 to about 10.0 mmol, preferably from about 1.0 to about 20.0 mmol of paramagnetic ion complex per kg of patient body weight.

The diagnostic compositions of the present invention are used in the conventional manner. The compositions may be administered to a patient, typically a warm-blooded animal, either systemically or locally to the organ or tissue to be imaged, and the patient then subjected to the MR imaging procedure. Protocols for imaging and instrument procedures are found in texts such as Stark, D. D.; Bradley, W. G. *Magnetic Resonance Imaging*; Mosby Year Book: St. Louis, Mo., 1992.

Radiopharmaceutical Imaging Procedures are found in Fred A. Mettler, Jr., M.D. M.P.H., Milton J. Guiberteau, M.D., *Essentials of Nuclear Medicine Imaging*, Grune and Stratton, Inc., New York, N.T. 1983) and E. Edmund Kim, M.S., M.D. and Thomas P. Haynie, M.D., (MacMillan Publishing Co. Inc., New York, N.Y. 1987).

XRCM Imaging Procedures are found in Albert A. Moss, M.D., Gordon Gamsu, M.D., and Harry K. Genant, M.D., *Computed Tomography of the Body*, (W. B. Saunders Company, Philadelphia, Pa., 1992) and M. Sovak, Editor, *Radiocontrast Agents*, (Springer-Verlag, Berlin 1984).

In another facet of the present invention, there is provided new ligands which have application (after complexing with, for example, a paramagnetic ion) in the MRI area. These ligands have the general formula set forth in II above.

In still another facet of the present invention, there is provided new precursors (sometimes referred to as "precursors"herein) to the ligands (of formula II) and which have the general formula set forth in I above.

Examples of the type of compounds falling within formulae I, II and III are set forth in Table I below.

TABLE 1

| Formula No. | M | $M^{11}$ | R | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|---|---|---|
| III (a) | Gd | — | H | SO | H | H | H | H | H | H | H | H | H | — |
| III (b) | Lu | — | H | SO | H | H | H | H | H | H | H | H | H | — |
| III (c) | Nd | — | H | S | $CH_3$ | H | H | $CH_3$ | H | H | $CH_3$ | H | H | — |
| III (d) | Gd | — | H | S | $NH_2$ | H | $OCH_3$ | H | H | H | $NH_2$ | H | $OCH_3$ | — |
| III (e) | Lm | — | $PO_3Na_2$ | SO | COONa | COONa | H | COONa | COONa | H | COONa | COONa | H | — |
| II (a) | — | Na | peptide | SO | H | H | H | $NH_2$ | H | H | H | H | $NH_2$ | — |
| II (b) | — | Li | glucose | S | $OCH_3$ | $NH_2$ | H | $OCH_3$ | $NH_2$ | H | $OCH_3$ | $NH_2$ | H | — |
| II (c) | — | K | $C_2H_5$ | SO | H | H | $CH_3$ | H | H | $CH_3$ | H | H | $CH_3$ | — |
| II (d) | — | K | H | SO | $CH_3$ | H | H | $NH_2$ | H | H | COONa | H | H | — |

TABLE 1-continued

| Formula No. | M | M$^{11}$ | R | R$_1$ | R$_2$ | R$_3$ | R$_4$ | R$_5$ | R$_6$ | R$_7$ | R$_8$ | R$_9$ | R$_{10}$ | R$_{11}$ |
|---|---|---|---|---|---|---|---|---|---|---|---|---|---|---|
| I (a) | — | — | — | — | H | H | H | H | H | H | H | H | H | COH |
| I (b) | — | — | — | — | CH$_3$ | H | OCH$_3$ | H | NH$_2$ | H | COONa | H | H | P |
| I (c) | — | — | — | — | COONa | NH$_2$ | H | OCH$_3$ | NH$_2$ | CH$_3$ | H | H | H | COCH$_3$ |

A class of preferred compounds has the formula

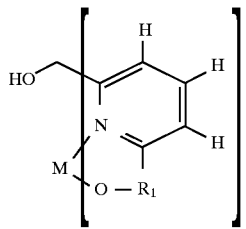

wherein R$_1$ is S or SO, and M is a metal ion of the lanthanide series having an atomic number 57–71 or a transition metal of an atomic number 21–29, 42 or 44.

The novel precursors, novel ligands and the novel ligand-metal complexes of the present invention are prepared from substituted aromatic heterocycles ("SAH") which are generally commercially available from Aldrich Chemical Company (Milwaukee). The SAH have the general formula:

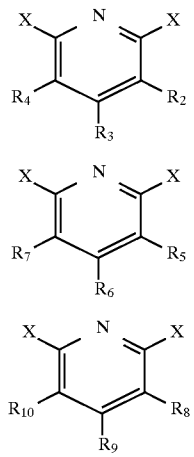

wherein R$_2$–R$_{10}$ are the same as defined herein and X is halogen such as Cl, Br, and I.

When R$_2$, R$_3$ and R$_4$ are the same as R$_7$, R$_8$ and R$_9$ and/or R$_8$, R$_9$ and R$_{10}$, then SAH of formulae A, B, and C are the same. When A, B, and/or C are different, i.e. the substituents are different, then equivalent moles of each must be used in order to prepare the desired precursors, ligands and/or metal-ligand complexes. For example, when A, B, and C are all the same, X is halogen (such as Br) and then a halogen lithium exchange reaction is carried out at low temperature (e.g. from about –100° C. to about 20° C.) to generate a monolithium reagent, which is then coupled with a linking reagent such as POCl$_3$, PCl$_3$, methyl chloroformate or diphenylcarbonate to link three units of SAH to form a capping mode ligand in one or two steps as shown in Schemes 1 and 2. The other halogen atom on the SAH is replaced in order to introduce the SH group in one or more steps, also shown in Scheme 2.

Scheme 3 represents the situation where R$_2$–R$_{10}$ are different, as discussed above with reference to formulae A, B, and C. In this case, the following general procedure is carried out.

2,6-dihalo-3-R$_5$-4-R$_6$-5-R$_7$-pyridine (7) is slurried in diethyl ether and cooled to –70° C. One equivalent of butyllithium in hexane is added dropwise. The resulting slurry is stirred at –70° C. until a clear solution (9) is obtained. Transfer the resulting solution (9) through a cannula to a reaction flask containing an ether solution of methyl 2-halo-3-R$_2$-4-R$_3$-5-R$_4$-picolinate (1) at –70° C. The resulting solution is stirred at –70° C. for one hour and then allowed to warm to –10° C. when it is quenched with NH$_4$Cl/H$_2$O. The volume of the ether is reduced to ⅓ of the original to cause precipitation of the product (2). The precipitate is filtered and dried.

Solution (10) is generated with the same procedure as described for (9). (9) is then transferred to a flask containing an ether solution of (2) at –70° C. The resulting solution is stirred at –70° C. for one hour and then allowed to warm to –10° C. when it is quenched with NH$_4$Cl/H$_2$O. The volume of the ether is reduced to ⅓ of the original to cause precipitation of the product (3). The precipitate was filter and dried.

A one liter 3-neck schlenk flask, equipped with a stirbar, is charged (3) under nitrogen atmosphere. Anhydrous DMF is added to dissolve (3). In a beaker, sodium thiomethoxide (18 eq) is slurried with DMF. The slurry is then slowly added to the solution of (3) with stirring. A blue solution is obtained and it is very hot. The center neck is then stoppered and a thermowell/adapter placed in a side neck. After sealing the sidearm stopcock, the flask is removed from the box, and placed under nitrogen. A reflux condenser is placed on the center neck. The solution is refluxed for 6–7 hours with stirring. The blue color disappears after 1 hour. After reflux, the solution is cooled with a bath and titrated to a pH of about 6 from an initial pH of >14, with conc. HCl solution. Salt is filtered and filtrate concentrated. Water is added to break up any gummy residue to give a yellow solid, which is filtered, washed with water and dried to yield (4) in quantitative yield.

The mercato compounds (4) are oxidized to the sulfenate compounds (5) by oxygen in anhydrous DMF and LiOH. (4) are also oxidized to the sulfinate compounds by forming sodium salts first with NaOH and then two equivalents of hydrogen peroxide.

Scheme 1

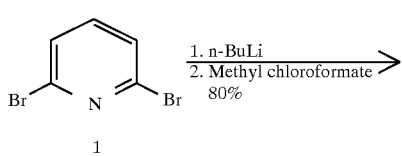

-continued
Scheme 1
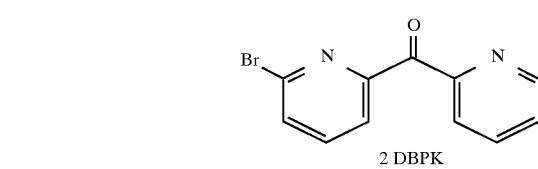
2 DBPK
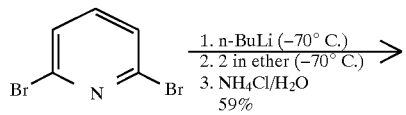
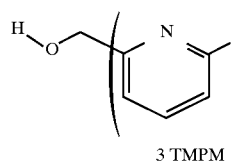
3 TMPM
Scheme 2
Synthesis of GdTSPM, GdTSIPM and GdTSEPM
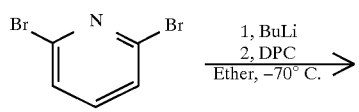
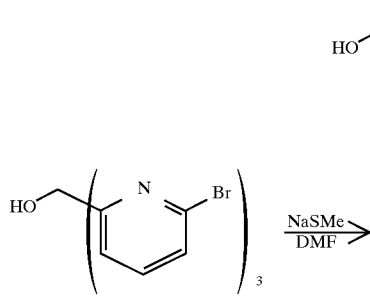
-continued
Scheme 2
Synthesis of GdTSPM, GdTSIPM and GdTSEPM
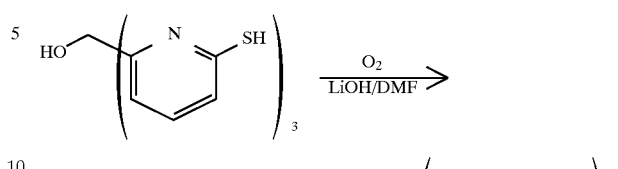
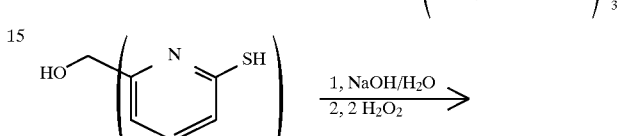
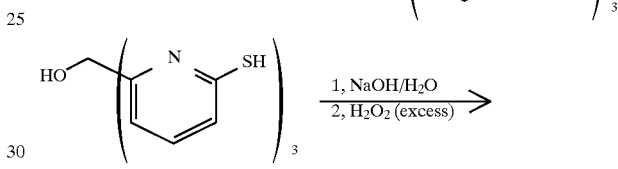
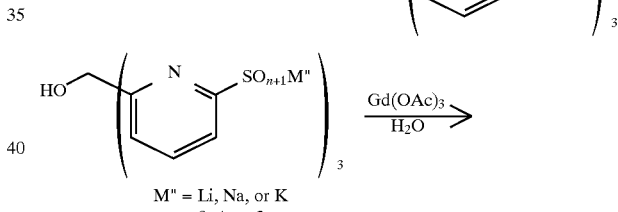
M" = Li, Na, or K
n = 0, 1, or 2
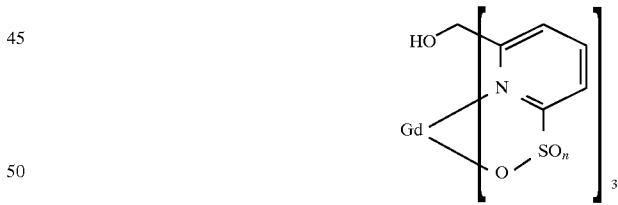

Scheme 3

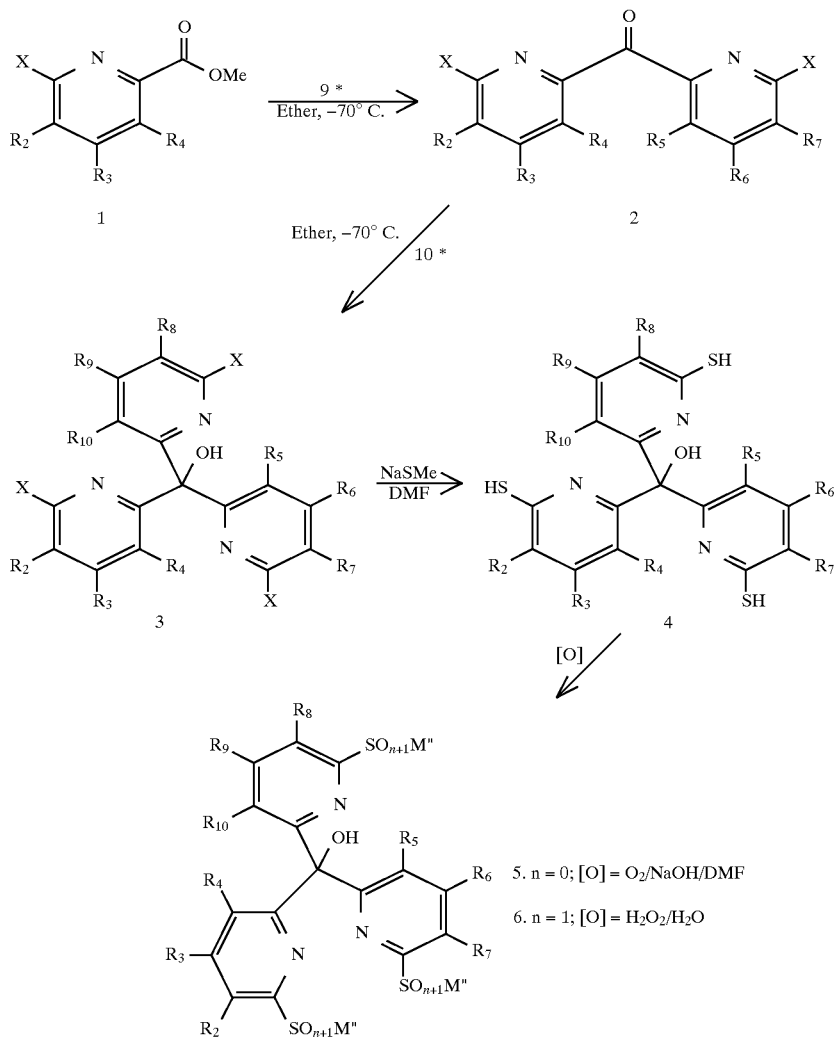

5. n = 0; [O] = $O_2$/NaOH/DMF
6. n = 1; [O] = $H_2O_2/H_2O$

\* 9 and 10 are generated as follows:

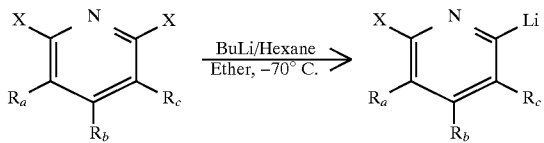

7. a = 5, b = 6, c = 7
8. a = 8, b = 9, c = 10

9. a = 5, b = 6, c = 7
10. a = 8, b = 9, c = 1

The final step in the overall synthesis for preparing the ligand-metal complex is reaction of the novel ligand with a solution containing the metal ion in the form of a compound which, for example, may be the acetate form, e.g. Gd(OAc)$_3$. The pressures (e.g. atmospheric) and temperatures (e.g. 30° C. –100° C.) are suitable. The mole ratio of ligand to metal (atom) is from about 5:1 to about 4:1, preferably about 1:1.

Some examples of specific processes for preparing the novel compositions (formula I, II, and III) of the present invention are set forth in Schemes 1, 2, and 3 and which, respectively, outline the detailed procedures described in Examples 1–5.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Step (a) Process for the synthesis of tris(2-bromo-6-pyridyl) methanol(TBPM)

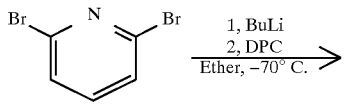

Anhydrous diethylether (400 ml) and 2,6-dibromopyridine (38 g, 0.16 mol) were charged into a one-liter three-neck Schlenk flask, equipped with stirbar, a 125 ml addition funnel, a thermocouple adapter and a septum. Diphenylcarbonate (10.3 g, 0.048 mol) and diethylether (60 ml) were charged into the addition funnel. The setup was then removed from the box and placed under nitrogen. The flask was cooled with a −70° C. dry-ice acetone bath. When the temperature inside the flask reached −70° C., butyllithium (100 ml, 1.6M in n-hexane) was added through a cannula in such a rate that the temperature was maintained at below −70° C. The solution was stirred for an additional hour at −70° C. and a homogeneous light yellow solution was obtained. Diphenylcarbonate solution was then added in such a rate that the temperature was maintained at −70° C. The solution turned into a dark purple color. Stirring was continued at −70° C. for an additional hour before the cooling bath was removed. The solution was quenched with ammonium chloride (9.5 g, 0.18 mol) in 30 ml of water when the temperature of the solution reached −20° C. The solution turned to a light brown color with precipitate, which was filtered and washed with water. A second batch of product was obtained by evaporating organic solvent from the filtrate. Combined yield after drying was 17.5 g, 65.5%.

Step (b): Process for the synthesis of tris(2-mercapto-6-pyridyl)methanol (TMPM)

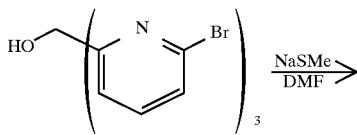

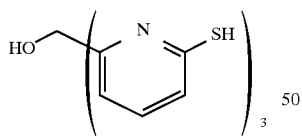

A 250 ml 3-neck schlenk flask, equipped with a stirbar, was charged with 5 grams (0.01 mol) of tris(2-bromo-6-pyridyl) methanol (TBPM) under nitrogen atmosphere. Anhydrous DMF (100 ml) was added to dissolve TBPM. In a 250 ml beaker, sodium thiomethoxide 12.61 g. (0.1 8mol, 18eq) was slurried with 60 ml of DMF. The slurry was then slowly added to the TBPM solution with stirring. A blue solution was obtained and it was very hot. The center neck was then stoppered and a thermowell/adapter placed in a side neck. After sealing the sidearm stopcock, the flask was removed from the box, placed under nitrogen. A reflux condenser was placed on the center neck. The solution was refluxed for 6–7 hours with stirring. A blue color disappeared after 1 hour. After reflux, the solution was cooled with an ice bath and titrated to a pH of about 6 from a initial pH of >14, with conc. HCl solution. Salt was filtered and filtrate concentrated. Water (200 ml) was added to break up the gummy residue to give a yellow solid, which was filtered, washed with water and dried to yield 3.76 g of yellow powder. This is 104% based on the formula weight, due, most likely, to small amount of salt and solvents trapped in the solid.

EXAMPLE 2

Process for the synthesis of tris(2-mercapto-6-pyridyl) phosphine

Thiourea (2.83 g, 37.2 mmol) and tris(6-bromo-2-pyridyl) phosphine (4.99 g, 9.9 mmol) were charged into a 100 ml flask equipped with nitrogen purge, and a stir bar. Acetic acid (47 ml) was added and the slurry was heated to 60° C. to obtain a yellow solution, which was heated at 60° C. overnight. Clumps of solid was formed and filter at 60° C. The solid (about 6.0 g wet) was dissolved in 50 ml of water and the solution was filtered to reduce the cloudiness. NaOH (50%, 7.5 g) was added and solution stirred at room temperature overnight. The solution was then acidified with 6N HCl to pH 1–2, resulting precipitation of yellow solid, which was filter and dried in a vacuum oven at 60° C. $^{31}$P NMR (D$_2$O, 162 MHZ), δ: −5.87. $^1$H NMR (D$_2$O, 400 MHZ), δ: 5.74 (1,d,J$_{H-H}$=8.0 Hz); 6.94 (1,d,J$_{H-H}$=8.0 Hz). $^{13}$C NMR (D$_2$O 100 MHZ), δ: 121.59; 128.94, (d, J$_{C-P}$=6.0 Hz); 135.72 (d, J$_{C-P}$=22.0 Hz); 159.26 (d, J$_{C-P}$=8.0 Hz); 172.09 (d, J$_{C-P}$=15.0 Hz).

EXAMPLE 3

Synthesis of lithium tris (2-sulfenate-6-pyridyl) methanol (LiTSEPM) (n=1 in structure below)

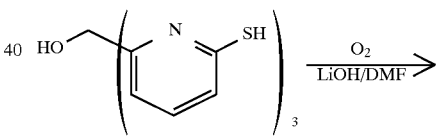

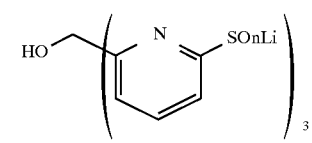

n = 1 and 3

Tris (2-mercapto-6-pyridyl) methanol (TMPM) (1.0 g) and 100 ml DMF were charged into a 250 ml 2-neck flask equipped with a stirbar, a sparge tube and a center 1 psi backpressure fitting. Granular LiOH (0.87 g, 13 eq.) was then added and the mixture was stirred while sparging with O$_2$ intermittently. The O$_2$ pressure was maintained at 1 psi above atmosphere during sparging by the check valve mounted on the flask. After 24 hrs, a slightly yellow slurry was formed, which was decanted from remaining MOH. The slurry was filtered and the solid obtained was washed with ethanol. The solid, which contained two products, the sulfenate and sulfonate in 90:10 ratios. The yield of LiTSEPM was about 50%. $^1$H NMR (400 MHz, D$_2$O ) : 7.64 (3, d, J$_{H-H}$=8 Hz). $^{13}$C NMR (100 MHz, D$_2$O ) δ: 82.7, 120.5, 125.9, 139.8, 158.0, 161.6, 7.83 (3,d, J$_{H-H}$=8 Hz), 7.96 (3,t,J$_{H-H}$=8 Hz).

EXAMPLE 4

Synthesis of sodium tris (2-sulfinate-6-pyridyl)methanol (NaTSIPM)

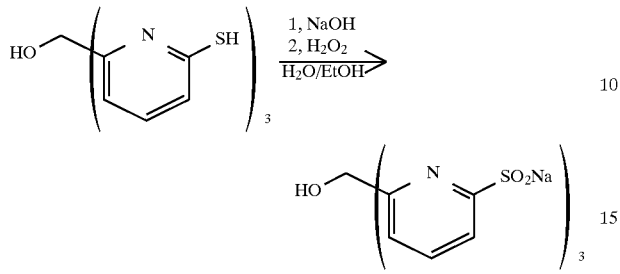

Tris (6-mercapto-6-pyridyl) methanol (0.25 g, 0.70 mmol) was charged into a 100 ml reaction flask equipped with a stirbar. A solution of NaOH (0.235 g) in 20 ml water/ethanol (1:1) was added. The yellow solid did not dissolve. Hydrogen peroxide (0.4 g, 4.1 mmol) was added dropwise. Solid still did not dissolve, but color became lighter. The slurry was stirred for 2 hours at room temperature and then evaporated under vacuum at about 65° C. to dryness. The white solid obtained, which was soluble in water, was determined by NMR to be NaTSIPM. Yield, 0.43 g, quantative. $^1$H NMR (440 MHz, D$_2$) δ: 7.73 (6, d, $J_{H-H}$=4 Hz), 7.95 (3, t, $J_{H-H}$=4 Hz). $^{13}$C NMR (100 MHz, D$_2$O) δ: 83.4, 118.6, 124.2, 139.1, 156.7, 165.4.

EXAMPLE 5

Synthesis of Gadolinium tris(2-sulfenate-6-pyridyl) methanol (GdTSEPM) and gadolinium tris(2-sulfinate-6-pyridyl)methanol (GdTSIPM)

LiTSEPM (0.5 g, 90%, 1.1 mmol) was dissolved in 5 ml of water and mixed with Gd(OAc)$_3$.4H$_2$O (0.45 g, 1.1 mmol) in 5 ml of water. The resulting solution was stirred at 65° C. for one hour. Volume of the solution was reduced under vacuum to about 2 ml. solution was cooled to room temperature to obtain 0.3 g crystalline white powder. Yield, 48%. The formation of the complex was followed by using capillary zone electrophoresis. GdTSIPM was synthesized similarly.

What is claimed is:

1. A process of performing an MR imaging diagnostic procedure in a patient in need of the same comprising administering to the patient an effective amount of an MR imaging diagnostic medium and then exposing the patient to an MR imaging measurement step to which the diagnostic medium is responsive thereby imaging at least a portion of the patient's body, wherein the diagnostic medium comprises a composition of matter which contains a compound which has the structural formula:

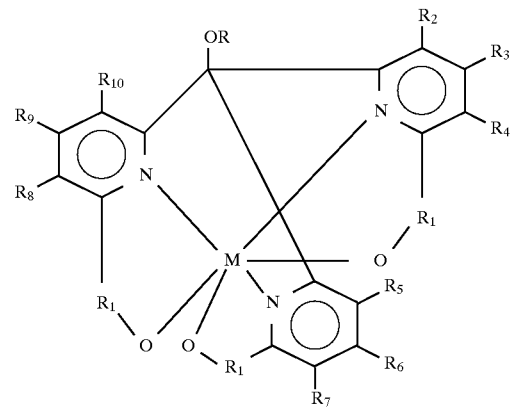

wherein:
M is a suitable metal ion,
R$_1$ is S, S(O)$_n$ where n is 1
R$_2$–R$_{10}$ are each independently selected from the group consisting of
  (a) R
  (b) OR
  (c) N(R)$_2$
  (d) NHC(O)R
  (e) COO$^-$ M'
  (f) C(O)N(R)$_2$, and
  (g) SO$_3^-$ M'
wherein R is selected from the group consisting of
  (I) H
  (ii) C$_1$–C$_{20}$ alkyl
  (iii) hydroxyalkyl (C$_1$–C$_{30}$)
  (iv) CH$_2$CH(OH)CH$_2$ (O CH$_2$CH(OH)CH$_2$)$_n$OH (n=0–10)
  (v) CH$_2$CH$_2$ (O CH$_2$CH$_2$)$_n$OH (n=0–10)
  (vi) ribose
  (vii) glucose
  (viii) peptide or polypeptide, and
  (ix) PO$_3^{2-}$ 2M'
and M' is Na$^+$ or meglumine.

2. The process as set forth in claim 1 wherein M is a metal ion of the lanthanide series having an atomic number of 57–71 or a transition metal of an atomic number of 21–29, 42 or 44.

3. The process as set forth in claim 1 wherein at least one of R$_2$–R$_{10}$ is hydrogen.

4. The process as set forth in claim 1 wherein at least one of R$_2$–R$_{10}$ is CH$_3$.

5. The process as set forth in claim 1 wherein at least one of R$_2$–R$_{10}$ is OCH$_3$.

6. The process as set forth in claim 1 wherein at least one of R$_2$–R$_{10}$ is NH$_2$.

7. The process as set forth in claim 1 wherein at least one of R$_2$–R$_{10}$ is COONa.

8. The process as set forth in claim 1 wherein R is hydrogen.

9. The process as set forth in claim 1 wherein R is PO$_3$Na$_2$.

10. The process as set forth in claim 1 wherein R is peptide.

11. The process as set forth in claim 1 wherein R is glucose.

12. The process as set forth in claim 1 wherein R is C$_2$H$_5$.

13. The process as set forth in claim 1 wherein M is selected from the group consisting of chromium (III), manganese (II), iron (III), iron (II), cobalt (II), nickel (II), copper (II), praseodymium (III), neodymium (III), samarium (III), ytterbium (III), gadolinium (III), terbium (III), dysprosium (III), holmium (III), erbium (III), lanthanum (III), gold (III), lead (II), bismuth (III), lutetium (III), and europium (III).

14. The process as set forth in claim 1 wherein M is gadolinium (III).

15. The process as set forth in claim 1 wherein M is lutetium (III).

16. The process as set forth in claim 1 wherein $R_1$ is S.

17. The process as set forth in claim 1 wherein $R_1$ is SO.

18. The process as set forth in claim 1 wherein the composition has the formula

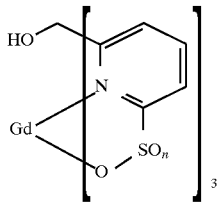

wherein n is 0 or 1.

19. The process as set forth in claim 1 wherein the composition has the formula

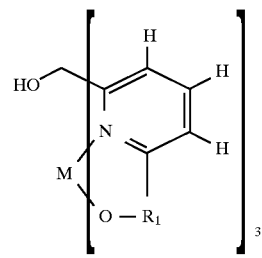

wherein:

$R_1$ is S or SO.

M is a metal ion of the lanthanide series having an atomic number 57–71 or a transition metal of an atomic number 21–29, 42 or 44.

20. The process as set forth in claim 19 wherein M is gadolinium or lutetium.

* * * * *